(12) United States Patent
Sussman

(10) Patent No.: US 8,920,792 B1
(45) Date of Patent: Dec. 30, 2014

(54) INJECTION OF COLLAGENASE IN THE TREATMENT OF HERNIATED MENISCUS

(71) Applicant: Bernard Sussman, Washington, DC (US)

(72) Inventor: Bernard Sussman, Washington, DC (US)

(*) Notice: Subject to any disclaimer, the term of this patent is extended or adjusted under 35 U.S.C. 154(b) by 0 days.

(21) Appl. No.: 14/067,588

(22) Filed: Oct. 30, 2013

(51) Int. Cl.
*A61K 38/43* (2006.01)
*A61K 38/48* (2006.01)
*A61K 9/00* (2006.01)
*A61B 5/055* (2006.01)
*A61B 8/08* (2006.01)

(52) U.S. Cl.
CPC ............ *A61K 38/4886* (2013.01); *A61K 9/0019* (2013.01); *A61B 5/055* (2013.01); *A61B 8/0841* (2013.01)
USPC .......................................................... 424/94.1

(58) Field of Classification Search
None
See application file for complete search history.

(56) References Cited

U.S. PATENT DOCUMENTS 5,833,685 A * 11/1998 Tortal et al. ..................... 606/23
2008/0145357 A1 * 6/2008 Story et al. ................. 424/94.67

* cited by examiner

*Primary Examiner* — Albert Navarro
(74) *Attorney, Agent, or Firm* — Andrew C. Aitken

(57) ABSTRACT

A method of treating a human patient having a herniated meniscus is disclosed that includes first identifying the precise location of the herniated meniscus fragment and then injecting a therapeutically effective amount of collagenase *clostridium histolyticum* directly into the tissue using a hypodermic needle and syringe to dissolve the fragment.

8 Claims, No Drawings

INJECTION OF COLLAGENASE IN THE TREATMENT OF HERNIATED MENISCUS

FIELD OF THE INVENTION

This invention relates to the treatment of a torn or herniated meniscus of humans and relates more particularly to a treatment method whereby herniated cartilage of the meniscus is solubilized in vivo to relieve inflammation and interference with the smooth operation of the knee joint without resort to surgical removal of the displaced part.

BACKGROUND OF THE INVENTION

The knee joint has been described as the most complex joint of the human body. It contains four ligaments each limiting a specific directional movement and two fibrocartilagenous eccentric plates forming meniscus cartilage. The meniscus cartilage is made up of C-shaped fibrocartilage tissue located within the knee joint. The menisci, named the lateral meniscus and the medial meniscus are two tough pieces of fibrocartilage that rest between the femur and the tibia. Combined, these two menisci bear all of the weight of the body when an individual is standing. The cartilage allows the tibia and femur bones to slide over one another reducing friction between the bones and prevents damage from wear and tear. The meniscus cartilage also acts as a shock absorber preventing the bones smashing against each other with impact and functions as a stabilizer. However well designed it may be for ordinary movements, the meniscus is often no match for the uncertainties of a fall much less the rigors of modern everyday sports activities. A common injury of the knee is when the meniscus cartilage tears, or herniates with partial or complete extrusion of the meniscus. The tearing of the meniscus can result in swelling, inflammation and pain. The torn portion may also interfere with mechanical operation of the joint wherein the knee is locked.

At the present time, most meniscus tears are addressed using arthroscopic surgery techniques where surgeons repair or remove the herniated section. The partial removal of the meniscus—called a partial meniscectomy—using arthroscopic surgery causes less trauma to surrounding tissue than conventional surgical techniques. A partial meniscectomy is performed to remove only the herniated segment of the meniscus. This procedure has been reported to be successful over the short, and long term if the meniscus tear is relatively small. But for some large meniscus tears, a sufficient portion of the meniscus is removed such that problems will remain and long term prognosis is not optimal. Arthroscopic surgery can thus treat the wear and tear injuries related to a torn meniscus, which is the crescent-shaped cartilage that cushions the knee, as well as injuries to the surface of bone that makes joint movement painful. In lavage and debridement procedures, the surgeon identifies floating or displaced tissue pieces and either flushes them out with a solution applied with arthroscopy or smoothes the exposed surfaces to try to decrease pain.

Conventional meniscus repair surgery is conducted through the visualization offered by the lighted arthroscope that allows the surgeon to follow the surgery on a television monitor. Instruments which have a thickness of about 0.15 in (4 mm) are inserted in a triangular fashion around the knee. The arthroscope is inserted in a first incision, and the instruments used to cut and/or smooth and to otherwise manipulate the tissue are inserted through the other incisions. In this fashion, the surgeon has magnification, perspective, and the ability to make tiny adjustments to the tissue without open surgery. The triangular approach is considered highly effective and safe.

While arthroscopic surgery is advantageous and preferred over prior conventional surgical techniques, it still involves relatively large incisions into the knee for both the scope and the retractor that is used to incise the torn meniscus part from the larger structure and remove it from the surgical field. Consequently, the recovery from the surgery can take up to three to four months and may require the use of knee brace to either totally immobilize the knee or significantly restrict motion, such as a hinged knee brace. In addition, after surgery crutches are typically required along with the administration of narcotics to treat pain. The application of ice packs is recommended to reduce swelling. There is also some risk of infection. Steroid therapy may be also be employed in conjunction with or after the surgery for its anti-inflammatory reaction and its reduction of edema. In addition to the treatment of meniscus tears, arthroscopic surgery is performed to remove loose bodies within the synovial joint which may comprise displaced cartilage.

While arthroscopic surgery has been a conventional technique to treat meniscal tears and the removal of loose bodies, there exists a need for alternative and less invasive manner in which to provide effective treatment. Post operative narcotics, prolonged knee cooling with a special device and extended physical therapy is usually required.

Collagenase is an enzyme found in certain clostridia culture filtrates, and more especially culture filtrates of *Clostridium histolyticum* and *Clostridium welchii*; the former being the preferred source. As initially recovered, collagenase is impure and contains not only collagenase but a peptidase and trypsin-like proteinase. Its recovery in impure form is described by Mandl et al (Isolation and Characterization of Proteinase and Collagenase from *Cl. histolyticum*, J. Clin. Invest., 32, 1323 (1953)).

Currently, collagenase is used for debridement of third degree burns, in enzymatic separation of dermis and epidermis (Whole Mounts for the Study of Skin and its Appendages, J. Invest. Dermatol., 23, 437-453 (1954)). Collagenase also has been used in studies of different collagens by electron microscopy (Evaluation of Structural and Chemical Changes in Connective Tissue, Annals N.Y. Acad. Sci., 56, 674-683 (1952)). Collagenase may be purified as by chromatography so as to recover an enzyme consisting essentially of collagenase. Moreover, by the employment of conventional techniques to remove bacteria, the collagenase may be produced in sterile form. Collagenase has been purified by electrophoresis of enzyme preparations obtained by ammonium sulfate fractionation and has been the subject of biological investigation by Mandl et al., *Clostridium Histolyticum Collagenase, Its Purification and Properties,* Archives of Biochem. and Biophysics, 74, 465-475 (1958)) wherein its activity has been studied in regards to its ability to attack collagen and its degradation products and its inability to attack protein substrates such as casein or hemoglobin or the fibrous proteins, fibrin, keratin and elastin.

Thus, collagenase may be provided in dosage form appropriate for a single internal injection into a living mammal and, to this end, a sterile, purified solution of collagenase is introduced into a vial in sufficient quantity to provide the necessary volume for injection of a solution having a concentration of approximately 0.01 to 0.1 percent. The solution is then subjected to lyophilization to produce the collagenase in dry, sterile condition and the vial is sealed. At the time of use the aqueous medium used for injection is added directly to the vial. As aforesaid, the aqueous solvent may contain a small amount of buffered saline and calcium phosphate to provide the desired pH. The collagenase solution is ready for use as soon as it is prepared in this way.

Known procedures for the purification of the collagenase have been reported for many years. For example a procedure was described by Keller and Mandl, The Preparation of Purified Collagenase, Arch. of Biochem. and Biophys., 101, 81 1963. Prior to clinical use, a test portion of the collagenase that is produced should be tested to insure its essential freedom from proteolytic and elastolytic activity. The materials should also be tested for sterility and pyrogenicity.

Collagenase is also presently available in from of an ointments under the brand name Collagenase Santyl® (collagenase) and has an approved indication for debriding chronic dermal ulcers and severely burned areas. It is manufactured by Biospecifics Technologies Corp., 35 Wilbur Street Lynbrook, N.Y. 11563. The ointment is a sterile enzymatic debriding ointment which contains 250 collagenase units per gram of white petrolatum USP.

Collagenase has also been approved for the treatment of Dupuytren's contracture, a disease affecting the ligaments of the hand. The condition is characterized by an abnormal collagen buildup that forms a cord in the palm of the hand. The enzyme, collagenase *clostridium histolyticum*, is sold under the trademark Xiaflex by Auxilium Pharmaceuticals, Inc., 640 Lee Road, Chesterbrook, Pa. 19087. Xiaflex is supplied in single-use glass vials containing 0.9 mg of collagenase *clostridium histolyticum* as a sterile, lyophilized powder for reconstitution. Sterile diluent for reconstitution is provided in the package in a single-use glass vial containing 3 mL of 0.3 mg/mL calcium chloride dihydrate in 0.9% sodium chloride.

Collagenase is also an investigational drug for the treatment of Peyronie's disease. In summary, the FDA has repeatedly found collagenase can be safely administered and its efficacy has been demonstrated in connection with a number of indications.

Collagenase has also been used experimentally for intervertebral discolysis. As reported by Sussman and Mann, *Experimental Intervertebral Discolysis with Collagenase*, Journal of Neurosurgery, Vol. XXXI, No. 6 pp. 628-635 (1969) collagenase was used in animal experimental studies. The paper reports that enzymatic dissolution of the nucleons pulposus and fibrocartilage of the intervertebral disc was consistently produced in dogs following local injection of collagenase. Id at 634. An initial clinical report discussing the results of a phase I trial involving human subjects was published in 1981, Sussman Bromley, Gomez, *Injection of Collagenase in the Treatment of Herniated Lumbar Disc*, JAMA Volume 245 No. 7 (Feb. 20, 1981) While denatured collagen is susceptible to many proteolytic enzymes, unaltered collagen is resistant to all common proteolytic enzymes. However, collagenase is reported to be a unique microbial enzyme as regards its capacity to attack native collagen under physiological conditions of pH and temperature. See also Sussman, Intervertebral Discolsysis with Collagenase, Journal of the National Medical Association, Vol. 60. No. 3 pp 184-187 (May 1968); See also U.S. Pat. No. 3,678,158 to Sussman, Treatment of Herniated Intervertebral Discs of Mammals.

Also relevant to the present invention are advancements in guided injection technology. While both CT and MRI have been used to guide injections, the associated radiation and considerable expense make these methods difficult for patients, doctors and staff. Further, CT and MRI techniques sometimes require the addition of iodine based contrast agents and cannot quickly capture the real-time motion of a needle. With the advent of ultrasonic needle guiding technology it is now possible to accurately inject medication in small joints. For example, in Botwin, Sharma, Salidba and Patel, *Ultrasound-Guided Trigger Point Injections in the Cervicothoracic Musculature: A New and Unreported Technique*, Pain Physician 2008; 11:885-889, ISSN 1533-3159, the authors report that ultrasound—guided trigger point injections using Sonosite MicroMaxx compact ultrasound system can achieve proper needle placement within the cervicothoracic musculature.

Guided injection systems are commercially available and marketed by, inter alia Fisher Biomedical, Inc. 740 Commerce Drive Suite 13, Venice Fla. 34292 under the SIUI CTS-880 line including the CTS-8800; UMI, 832 Jury Court, San Jose Calif. 95112 which markets the Sonosite M-Turbo Ultrasound that includes needle visualization software. Yet a further provider of an ultrasound needle guided injection systems is Diagnostic Instruments Inc., Mindray North America which sells a device under the Mindray MSK M7 brand. See also Astourian, Patrick, Ultrasound guided musculoskeletal injections, 2011.

Thus, ultrasound guided injection has been used for the administration of corticosteroids and other pain relief medication. See *The Journal of Musculoskeletal Medicine*. Vol. 27 No. 9 Arthritis Rheum 2010, 62:1862-18. See also *The Journal of Musculoskeletal Medicine*. Vol. 26 No. 11 *J Rheumatol* 2009, 36:1892-1902 (addressing intra-articular injections performed with ultrasound image guidance.)

It is therefore an object of this invention to provide a new and effective relatively non-invasive treatment method for meniscus tears. It is a further object to obtain analogous results to those obtained by current arthroscopic surgical techniques by the selective dissolution of the torn or floating meniscus comprised of fibrocartilage with a therapeutically effective amount of collagenase.

SUMMARY OF THE INVENTION

According to the present invention a new treatment of the knee is disclosed using collagenase. The present treatment method targets the portion of the meniscus that has been torn or detached without injury to adjacent tissues, blood vessels or bone by the use of purified sterile collagenase that is injected directly into the meniscus fragment. As the result of the injection, the fibrocartilagenous tissue of the herniated meniscus is selectively dissolved. The herniated meniscus of the knee joint is thereby treated in situ and its selective dissolution is effected in vivo using a purified solution of collagenase that is injected directly into the herniated meniscus.

DETAILED DESCRIPTION AND EXAMPLES

In view of the past studies published in the prior art, and in particularly, studies directed to the intervertebral disc sections, it is apparent that collagenase will effectively dissolve fibrocartilage in vivo. Adjoining tissues such as blood vessels and muscles also contain collagen; but in such adjoining tissues the proportion of collagen relative to other tissue material that is not solubilized by collagenase is greater, and based upon in vivo studies the practice of the present invention with the collagenase enzyme will exert little physiological or chemical effect on such adjoining tissues and that there is virtually no damage to them as regards their integrity or their physiological functioning in the living mammal. Similarly, based upon previous reported studies the enzyme does not have any apparent adverse effect on the adjoining bone.

According to the present invention, collagenase is injected directly into herniated or floating meniscus of a human knee with a therapeutically effective amount of collagenase to allow substantial dissolution in vivo. For physiological usage in accordance with this invention, the enzyme can be recovered in the form of a purified stable solution thereof which is subjected to lyophilization to produce it in dry powder form. The dry powder is stable almost indefinitely. At room temperature a 0.1 percent solution is stable for 24 hours. Its stability is related to the concentration of the enzyme, pH and the type of buffer which is used with it. Activity is optimal at a pH of 6.4 but there is a range of activity between 6.2 and 7.8. Moreover, its zone of maximum activity is affected by the nature of any buffer that may be employed. When injected into the body of a mammal, the natural buffers of the body tend to maintain a pH of about 7.4 and when, and even though, the pH of the enzyme may differ from this pH the body buffers tend to bring the pH of an injected solution to a pH of approximately that of the body. As aforesaid, the activity of collagenase is high at the pH and temperature of the body. However, usually it is desirable to bring the pH of the solution that is injected to a pH adjacent that of the body by the use of some buffer such as a phosphate buffer or the conventional physiological saline solution, namely, a 0.85 percent solution of sodium chloride which has a pH of about 7. While ordinarily the activity of the enzyme does not have to be inhibited after injection, nevertheless its activity can readily be inhibited by the employment of cysteine, low pH, $10^{-2}$ M p-chloromercuric benzoic acid, $10^{-2}$ M iodo acetic acid and various horse antisera.

Reconstitution of the Lyophilized Powder
   a) Before use, remove a vial containing the lyophilized powder of and a vial containing the diluent for reconstitution from the refrigerator and allow the two vials to stand at room temperature for at least 15 minutes and no longer than 60 minutes. Visually inspect the vials to ensure that the cake of lyophilized powder should be intact and white in color.
   b) After removal of the caps from the vials, using aseptic technique swab the rubber stopper and surrounding surface of the vial containing lyophilized powder and that containing the diluent for reconstitution with sterile alcohol (no other antiseptics should be used).
   c) In the embodiment, the diluent for reconstitution contains calcium phosphate which increases the activity of lyophilized powder.
   d) Using a 1 mL syringe that contains 0.01 cc graduations with a 27-gauge ½-inch needle, withdraw 10 cc of the diluent.
   e) Inject the diluent slowly into the sides of the vial containing the lyophilized powder. Do not invert the vial or shake the solution. Slowly swirl the solution to ensure that all of the lyophilized powder has gone into solution.
   f) The reconstituted collagenase solution can be kept at room temperature (20° to 25° C./68° to 77° F.) for up to one hour or refrigerated at 2° to 8° C. (36° to 46° F.) for up to 4 hours prior to administration. If the reconstituted solution is refrigerated, allow this solution to return to room temperature for approximately 15 minutes before use.
   g) Discard the syringe and needle used for reconstitution and the diluent vial.

Preparation Prior to Injection
   a) The reconstituted lyophilized powder solution should be clear. Inspect the solution visually for particulate matter and discoloration prior to administration. If the solution contains particulates, is cloudy, or is discolored, do not inject the reconstituted solution.
   b) The administration of a local anesthetic agent injected into the dermis prior to the injection of collagenase is recommended.
   c) Apply an antiseptic at the site of the injections and allow the skin to dry.

Thus, in carrying out the invention, a purified and stable solution of collagenase, preferably about a 0.1 percent solution buffered to approximately 7 pH, is injected directly into the portion of the meniscus that has been separated from the body of the meniscus. In a first embodiment, in a first step, the location of the separated portion is identified using a MRI and the treating physician then orients the injection based upon the data from the MRI results. In alternative embodiments, the injection is guided by a radiologist who monitors the procedure using ultrasound, MRI or CT techniques.

In a contemplated embodiment the injection is administered by a radiologist using ultrasound, in a manner taught and disclosed by U.S. Pat. No. 8,007,487 which is incorporated by reference herein.

While the precise amount of solution injected will depend on the size of the disassociated or herniated meniscus part, in most instances, approximately 0.5 to 1.5 cc. is estimated to be sufficient. This estimate is based upon in vivo studies and in connection with human lumbar intervertebral disc therapy, whereas in the case of a human meniscus is a variable size, the injection may be of the order of about 0.5 to 5 cc. After the injection has been completed no further treatment is required other than such further observations as ordinarily are made in the nature of X-ray examination, pulse, temperature, urinalysis, etc.

For the purpose of providing a better understanding of this invention, it will be described herein below in connection with the following first examples that illustrate the efficacy of the material in connection with the dissolution of fibrocartilage with animal, human and in vitro applications.

Example 1

Collagenase according to the invention was successfully demonstrated to dissolve fibrocartilaginous material in ten dogs in the following manner. Each dog was first anaesthetized utilizing an intravenously administered short-acting barbiturate. Incursion was effected through the lower abdomen in nine cases and the paravertebral musculature in one case so as to afford operative retroperitoneal exposure and permit injection into the lumbar intervertebral disc space. In order to experimentally determine the safety of the treatment, the injection needle was advanced sufficiently so as to extend not only through the disc space but also just beyond and into the spinal canal but without penetrating the dura. 2 cc. of a 0.1 percent aqueous solution of purified, sterile collagenase solution were injected. Approximately 1 cc. of the solution remained in the disc space. The remaining cc. of solution was discharged into the spinal canal although there was some leakage through the needle opening upon withdrawal of the needle. The treatment was effected in this way so as to fully test the absence of adverse side effects on adjacent muscles, bone, blood vessels and more especially as regards possible contact with the dura.

For a period of 7 to 10 days following the injection each of the dogs remained fully ambulatory. Blood count, urinalysis, temperature and pulse all remained within normal limits. Moreover, there were no detectable neurological effects. After 7 to 10 days nine of the dogs and, after 2 days, one dog, were sacrificed and an X-ray of the treated portion of the spine was compared with a corresponding X-ray made prior to the injection. Moreover, the affected section of the vertebral column including adjoining vertebra was removed and cut in half so as to make the affected region available for sectioning and photographic and microscopic study. In each case it was observed that the nucleus pulposus and a major portion of the fibrocartilaginous material of the annulus were completely absent and that there had been no significant attack on the hyaline cartilage, the anterior or posterior ligaments, the adjacent bone or the dura.

Example 2

In a second example, during a laminectomy on a living human patient collagen material was removed from the disc space which responded to tests and microscopic examination identifying it as nucleus pulposus or annulus fibrosis with some admixture thereof. About ⅓ gram of the removed material consisting substantially entirely of nucleus pulposus was placed in 1 cc. of a 0.1 percent solution of purified collagenase in sterile aqueous solution. A like quantity consisting essentially of fibrocartilage was placed in a corresponding quantity of the 0.1 percent collagenase solution. Simultaneously a corresponding quantity of a small artery and of bone, respectively, were immersed in a corresponding quantity of the 0.1 percent collagenase solution in other vials. After 18 hours there was essentially complete dissolution of the nucleus pulposus and of the fibrocartilage whereas there was no detectable effect on either the artery or the bone. This example demonstrates the capacity of the collagenase to dissolve the nucleus pulposus and most of the fibrocartilage without detectable effect on adjacent blood vessels or bone.

Example 3

In another example, adjacent vertebral halves with a disc therebetween were removed from a human cadaver and subjected to dissection into component parts for enzymatic attack on material in the disc space. Under these conditions it is difficult to distinguish grossly between nucleus pulposus and degenerated fibrocartilage (annulus fibrosis). Nevertheless, in a separate test tube about ⅓ gram of nucleus pulposus, fibrocartilage, hyaline cartilage and anterior ligament, respectively, were immersed in 1 cc. of a 0.1 percent solution of purified collagenase. After 18 hours, dissolution of the nucleus pulposus and fibrocartilage was complete. Under similar conditions of contact with the 0.1 percent solution of collagenase the specimen of hyaline cartilage and the specimen of anterior ligament were not appreciably attacked.

Example 4

In yet another reported example, a disc specimen which had been obtained from a human cadaver and which was essentially similar to that described in example 3 was divided into five approximately equal parts. Each part was blotted with gauze and transferred to a sterile pre-weighed test tube. The tubes were reweighed thereby to obtain the weight of the sample and to each tube different relative amounts were added of a 0.1 percent solution of purified, sterile collagenase and of sterile 0.85 percent sodium chloride so as to achieve a range of four different concentrations of collagenase while maintaining the volume of added solution constant at 2.0 ml. The tubes were placed in a water bath at 37.degree.C. After seven hours the samples to which the collagenase solution had been added began to visually reveal the beginning stages of solubilization. At the end of 24 hours the solubilization observable as determined by visual inspection was substantial. The contents of each of the tubes were poured through gauze and the residues were blotted with gauze to the approximate state of moisture in the initial samples. The tubes were weighed and the percentage solubilization was determined. The data for the test samples and the test results showed that solubilization was substantial.

Example 5

A specimen of a herniated intervertebral disc removed from a living human patient during surgery was rinsed aseptically twice with sterile 0.85 percent sodium chloride to remove excess blood. The specimen was divided into five approximately equal parts which were treated identically according to the procedure described in example 5 to provide a range of four concentrations of collagenase while maintaining the volume of added solution constant at 2.0 mL The tubes were placed in a water bath at 37.degree.C. Solubilization was apparent after 2 or 3 hours and was very pronounced after seven hours. After 24 hours the contents of each tube was poured through gauze in an attempt to weigh the residue, as had been done in example 5. However, in each of the tubes containing enzyme solution the solubilization had progressed so far that any slight residue was not palpable and was impossible to weigh. Virtually all of the specimen was solubilized in each of the tubes containing enzyme solution.

The increase in solubilization as compared with example 4 reflects the greater collagenase content of the herniated disc used in example 5. The test data show that in the treatment of an herniated disc highly effective solubilization of the disc substance was obtained when employing a solution of the purified collagenase at concentrations of approximately 0.01 percent to approximately 0.1 percent.

In the treatment of human patients it is contemplated to effect entry into the knee joint space for injection of the collagenase solution from the lateral or anterolaterial section of the knee of the patient with the injection needle passing through the synovial membrane, and synovial fluid and into the herniated fragment of the meniscus. After injection, the patient is under no restrictions to resume activity. The efficacy of treatment can be monitored using subsequent MRI. In accordance with a first embodiment of the invention, after the herniated meniscus is diagnosed and the location of the herniated section is identified, 10 cc of collagenase is injected directly into the herniated portion. In accordance with a first embodiment, the physician uses an ultrasound equipment to guide the needle to the target fragment.

The present invention and its various advantages will be understood from the foregoing description and that it will be readily apparent to those ordinarily skilled in the art so that various changes may be made in form, construction and arrangement without departing from the spirit and scope of the invention.

I claim:

1. A method of treating a human patient having a herniated meniscus of the knee, comprising, identifying the location of said herniated portion of the meniscus and then injecting a therapeutically effective amount of collagenase *clostridium histolyticum* directly into said herniated meniscus tissue using a hypodermic needle and syringe to substantially break down said herniated portion.

2. The method of treatment recited in claim 1 wherein said therapeutically effective amount substantially completely dissolves said herniated meniscus tissue.

3. The method of treatment recited in claim 1 wherein said therapeutically effective amount is between 0.5 and 1.5 cc. of 0.1 percent solution of purified collagenase *clostridium histolyticum* in sterile aqueous solution.

4. The method of treatment recited in claim 3 wherein said sterile aqueous solution further comprises calcium phosphate.

5. The method of treatment recited in claim 1 wherein said therapeutically effective amount is between 0.5 and 5.0 cc. of 0.1 percent solution of purified collagenase *clostridium histolyticum* in sterile aqueous solution.

6. The method recited in claim 1 further comprising using imaging technology to guide said needle to said herniated portion during said injection step.

7. The method recited in claim 6 wherein said imaging technology comprises ultrasound.

8. The method recited in claim 1 wherein the location of the herniated meniscus is identified using an MRI imaging system.

\* \* \* \* \*